United States Patent
Wang et al.

(10) Patent No.: US 10,537,601 B2
(45) Date of Patent: Jan. 21, 2020

(54) **METHOD OF ISOLATING ANTI-VIRAL INGREDIENTS FROM *BAPHICACANTHUS CUSIA*, COMPOSITIONS COMPRISING THEM AND THEIR MEDICAL USE**

(71) Applicant: Macau University of Science and Technology, Taipa (MO)

(72) Inventors: Jing-Rong Wang, Taipa (MO); Zhi-Hong Jiang, Taipa (MO); Qi-Tong Feng, Taipa (MO); Guo-Yuan Zhu, Taipa (MO); Wei-Na Gao, Taipa (MO); Zifeng Yang, Taipa (MO); Nanshan Zhong, Taipa (MO)

(73) Assignee: MACAU UNIVERSITY OF SCIENCE AND TECHNOLOGY, Taipa (MO)

( * ) Notice: Subject to any disclaimer, the term of this patent is extended or adjusted under 35 U.S.C. 154(b) by 542 days.

(21) Appl. No.: 15/089,687

(22) Filed: Apr. 4, 2016

(65) Prior Publication Data

US 2017/0281702 A1    Oct. 5, 2017

(51) Int. Cl.
| | |
|---|---|
| *A61K 36/19* | (2006.01) |
| *A61K 31/47* | (2006.01) |
| *A61K 31/191* | (2006.01) |
| *A61K 31/192* | (2006.01) |
| *A61K 31/404* | (2006.01) |
| *A61K 31/517* | (2006.01) |
| *A61K 31/538* | (2006.01) |
| *A61K 31/7056* | (2006.01) |
| *A61K 31/567* | (2006.01) |

(52) U.S. Cl.
CPC ............ *A61K 36/19* (2013.01); *A61K 31/404* (2013.01); *A61K 31/538* (2013.01); *A61K 31/567* (2013.01); *A61K 2236/15* (2013.01); *A61K 2236/17* (2013.01); *A61K 2236/33* (2013.01); *A61K 2236/55* (2013.01)

(58) Field of Classification Search
CPC ................ A61K 31/538; A61K 31/517; A61K 31/7056; A61K 31/404; A61K 31/191; A61K 31/192; A61K 31/047; A61K 36/19; A61K 2236/15; A61K 2236/33; A61K 2236/55; A61K 2236/17; A61K 2236/30
USPC ......................................................... 514/27
See application file for complete search history.

(56) References Cited

PUBLICATIONS

Merck Manual, 16th Ed., 1992, pp. 183-189.*
Reutrakul et al, Planta Medica, 2006, 72, 1433-1435.*
Wang, P. et al, Marine Drugs, 2014, 12, 477-490.*
Qin Hua-Zhen et al, Chinese Archives of Traditional Chinese Medicine, 2009, 27(1), 168-169.*
Sun Xia-bing et al, Journal of Guangxi Teachers Education University—Natural Science Edition, 2008, 25(4), 66-69.*
Y. L. Ho, K. C. Kao, H. Y. Tsai, F. Y. Chueh, Y. S. Chang, "Evaluation of Antinociceptive, Anti-inflammatory and Antipyretic Effects of Strobilanthes cusia Leaf Extract in Male Mice and Rats", The American Journal of Chinese Medicine, vol. 31, No. 1, pp. 61-69, 2003.
T. Tanaka, T. Ikeda, M. Kaku, X. H. Zhu, M. Okawa, K. Yokomizo, M. Uyeda, T. Nohara, "A New Lignan Glycoside and Phenylethanoid Glycosides from Strobilanthes cusia BREMEK", Chem. Pharm. Bull. 52(10) 1242-1245 (2004), vol. 52, No. 10, pp. 1242-1245, Oct. 2004.
W. Gu, Y. Zhang, X. J. Hao, F. M. Yang, Q. Y, Sun, L. S. Morris-Natschke, L. Kuo-Hsiung, Y. H. Wang, C. L. Long, "Indole Alkaloid Glycosides from the Aerial Parts of Strobilanthes cusia", American Chemical Society and American Society of Pharmacognosy, J. Nat. Prod, 77, pp. 2590-2594, 2014.
Z. F. Yang, E. L. H. Leung, L. Liu, Z. H. Jiang, N. Zhong, "Developing influenza treatments using traditional Chinese medicine", Science/AAAS Custom Publishing Ofice, pp. 535-537, 2015.
M. S. Singh, P. Singh, S. Singh, "Synthesis of benzoxazole-2-one, benzothiazole-2-ones and their 2-thione derivatives: Efficient conversion of 2-thione to 2-oxo derivatives", Indian Journal of Chemistry, vol. 46B, pp. 1666-1671, Oct. 2007.
Y. Liu, Y. F. Ou, H. Y. Yu, L. Li, N. L. Wang, X. S. Yao, "Chemical constituents in the leaves of Baphicacan thus cusia (Nees) Bremek", Chinese Journal of Medicinal Chemistry, vol. 19, No. 4, pp. 241-283, Aug. 2008. English Abstract provides known compounds for which this reference has been cited.
F. A. Macias, D. Marin, B. A. Oliveros, D. Chinchilla, A. M. Simonet, J. M. Molinillo, "Isolation and Synthesis of Allelochemicals from Gramineae: Benzoxazinones and Related Compounds", J. Agic. Food Chem, vol. 54, No. 4, pp. 991-1000, 2006.
Y. H. Liu, G. W. Qin, Chin, S. P. Ding, X. Y. Wu, "Studies on chemical constituents in root of Isatis indigotixa(III)", Chinese Traditional and Herbal Drugs, vol. 33, No. 2, pp. 97-99, 2002. English Abstract provides known compounds for which this reference has been cited.
M. A. Ashour, E. S. Elkhayat, R. Ebel, R. Edrada, P. Proksch, Arkivoc, "Indole alkaloid from the Red Sea sponge *Hyrtios erectus*", ARKIVOC, pp. 225-231, 2007.
Y. Xiao, X. Kong, Z. Xu, C. Cao, G. Pang, Y. Shi, "Efficient synthesis of quinazoline-2, 4(1H,3H)—diones from CO2 catalyzed by N-heterocyclic carbine at atmospheric pressure", RSC Advances, vol. 5, pp. 5032-5037, 2014.

(Continued)

*Primary Examiner* — Ganapathy Krishnan
(74) *Attorney, Agent, or Firm* — Renner Kenner Greive Bobak Taylor & Weber

(57) ABSTRACT

The present invention provides a method of isolating at least one ingredient with anti-viral efficacy from *Baphicacanthus cusia*. The ingredient can be an alkaloid, a triterpenoid, a lignan, a phenylethanoid, a sesquiterpene lactone, or a flavonoid. Two new alkaloids are produced, which have not been previously reported. Moreover, the method isolates 12 compounds which could not or have not been previously isolated. A pharmaceutical composition includes the at least one ingredient and at least one pharmaceutical tolerable excipient. A method of treating a subject suffering from a viral disease includes administering at least one ingredient isolated from *Baphicacanthus cusia*.

5 Claims, 1 Drawing Sheet

(56) References Cited

PUBLICATIONS

Q. Ma, L. Hu, L. Kong, S. Huang, H. Dai, L. I. Yan, "Chemical constituents from the fungus *Ganoderma tropicum* (Jungh.) Bres. and their cytotoxic activities", African Journal of Microbiology Research, vol. 7, No. 16, pp. 1543-1547, 2013.

C. Ramesh, B. R. Raju, V. Kavala, C. W. Kuo, C. F. Yao, "A simple and facile route for the synthesis of 2H-1, 4-benzoxazin-2-(4H)-ones via reductive cyclization of 2-(2-nitrophenoxy) acetonitrile adducts in the presence of Fe/acetic acid", Tetrahedron, vol. 67, pp. 1187-1192, 2011.

M. E. Amer, M. I. Abou-Shoer, M. S. Abdel-Kader, A. El-Shaibany, N. A. Abdel-Salam, "Alkaloids and Flavone Acyl Glycosides from Acanthus arboreus", J. Brazil. Chem. Soc. vol. 15, No. 2, pp. 262-266, 2004.

S. M. Roopan, T. Maiyalagan, F. N. Khan, "Solvent-free syntheses of some quinazolin-4(3H)-ones derivatives", Can. J. Chem, vol. 86, pp. 1019-1025, 2008.

T. M. Potewar, S. A. Ingale, K. V. Srinivasan, "Synthesis of tryptanthrin and deoxyvasicinone by a regioselective lithiation-intramolecular electrophilic reaction approach", ARKIVOC, pp. 100-108, 2008.

J. Fotie, D. S. Bohle, M. L. Leimanis, E. Georges, G. Rukunga, A. E. Nkengfack, "Lupeol Long-Chain Fatty Acid Esters with Antimalarial Activity from Holarrhena floribunda", J. Nat. Prod, vol. 69, pp. 62-67, 2006.

S. Siddiqui, F. Hafeez, S. Begum, B. S. Siddiqui, "Oleanderol a New Pentacyclic Triterpene from the Leaves of Nerium oleander" Journal of Natural Product, vol. 51, No. 2, pp. 229-233, Mar.-Apr. 1988.

Z. I. Awan, K. A. Y. Habib-ur-Rehman, F. A. Minhas, "A New Lupan type Triterpene Butilinol from Viburnum grandiflorum", IOSR Journal of Applied Chemistry, vol. 51, No. 4, pp. 58-66, Sep.-Oct. 2013.

M. G. V. Silva, I. G. P. Vieira, F. N. P. Mendes, I. L. Albuquerque, R. N. D. Santos, F. O. Silva, S. M. Morais, "Variation of Ursolic Acid Content in Eight *Ocimum* Species from Northeastern Brazil", Molecules, vol. 13, pp. 2482-2484, 2008.

M. Abdel-Mogib, "A lupane triterpenoid from Maerua oblongifolia", Phytochemistry, vol. 51, pp. 445-448, 1999.

T. Shoko, I. Yoko, K. Eri, T. Yoshie, I. Hideyuki, H. Tsutomu, H. Sakagami, H. Tokuda, H. Nishino, D. Sugita, S. Shimura, T. Yoshida, "Production of bioactive triterpenes by Eriobotrya japonica calli", Phytochemistry, vol. 59, pp. 315-323, 2002.

U. U. Pateh, A. K. Haruna, M. Garba, I. Iliya, I. M. Sule, M. S. Abubakar, A. A. Ambi, "Isolation of Stigmasterol, β-Sitosterol and 2-Hydroxyhexadecanoic Acid methyl Ester From the Rhizomes of Stylochiton Lancifolius Pyer and Kotchy(Araceae)", Nigerian Journal of Pharmaceutical Science, vol. 8, No. 1, pp. 19-25, 2009.

G. Li, B. Li, G. Liu, G. Zhang, "Sterols from Aspergillus ochraceus 43" Chin. J. Appl. Environ. Biol, vol. 11, pp. 67-70, 2005.

G. Sun, X. Zhang, X. D. Xu, J. S. Yang, L. X. Lv, M. Zhong, "The isolation and structure identification of four Lignan", Journal of Medicinal Plants Research, vol. 6, No. 11, pp. 2200-2205, Mar. 23, 2012.

H. Shibuya, Y. Takeda, R. S. Zhang, A. Tanitame, Y. L. Tsai, I. Kitagawa, "Indonesian Medicinal Plants. IV. On the Constituents of the Bark of Fagara rhetza (Rutaceae). (2). Lignan Glycosides and Two Apioglucosides", Chem. Pharm. Bull, vol. 40, No. 10, pp. 2639-2646, 1992.

R. W. Owen, W. Mier, A. Giacosa, W. E. Hull, B. Spiegelhalder, H. Bartsch, Clin, "-Identification of Lignans as Major Components in the Phenolic Fraction of Olive Oil", Clinical Chemistry, vol. 46, No. 7, pp. 976-988, 2000.

A. Sandoval, E. Arias-Barrau, F. Bermejo, L. Canedo, G. Naharro, E. R. Olivera, J. M. Luengo, "Production of 3-hydroxy-n-phenylalkanoic acids by a genetically engineered strain of Pseudomonas putida", Appl Microbiol Biotechnol, vol. 67, No. 97, pp. 97-105, 2005.

H. Kobayashi, H. Oguchi, N. Takizawa, T. Miyase, A. Ueno, K. Usmanghani, M. Ahmad, "New Phenylethanoid Glycosides from Cistanche tubulosa (SCHRENK) HOOK. f. 1." Chem. Pharm. Bull, vol. 35, No. 8, pp. 3309-3314, 1987.

K. Machida, M. Kikuchi, "Norisoprenoids from Viburnum dilatatum", Phytochemistry, vol. 41, No. 5, pp. 1333-1336, 1996.

X. C. Weng, W. Wang, "Antioxidant activity of compounds isolated from Salvia plebeian", Food Chemistry, vol. 71, pp. 489-493, 2000.

J. E. Kinjo, K. Yokomizo, Y. Awata, M. Shibata, T. Nohara, "Structures of phytotoxins, AV-toxins C, D and E, produced by zonate leaf spot fungus of mulberry", Tetrahedron Letters, vol. 28, No. 32, pp. 3697-2698, 1987.

P. L. Wu, Y. L. Hsu, C. W. Jao, "Indole Alkaloids from Cephalanceropsis gracilis", J. Nat. Prod, vol. 69, pp. 1467-1470, 2006.

\* cited by examiner

METHOD OF ISOLATING ANTI-VIRAL INGREDIENTS FROM *BAPHICACANTHUS CUSIA*, COMPOSITIONS COMPRISING THEM AND THEIR MEDICAL USE

TECHNICAL FIELD

The present invention provides a method of isolating at least one ingredient in particular an ingredient with anti-viral efficacy selected from the group consisting of an alkaloid, a triterpenoid, a lignan, a phenylethanoid, a sesquiterpene lactone and a flavonoid from *Baphicacanthus cusia*. The present invention further refers to a composition, in particular a pharmaceutical composition comprising the at least one ingredient and at least one excipient. Still further, the present invention refers to a method of treating a subject suffering from a viral disease by administering at least one ingredient isolated from *Baphicacanthus cusia*. In accordance with the invention is also a method of treating a subject suffering from a viral disease by administering at least one compound having certain chemical formula to the subject.

BACKGROUND OF THE INVENTION

Influenza, which is also known as "flu", is a severe infectious disease associated with symptoms ranging from mild to severe and causes an annual world-wide death toll of about 250,000 to 500,000 people. The influenza virus annually affects from about 5 to about 15 percent of the population causing acute respiratory diseases. In particular, young, elderly patients and also patients suffering from chronic diseases are at high risk and in particular may be threatened by accompanying severe bacterial infections like pneumonia.

Influenza viruses can be categorized into three types, namely types A, B and C. The type A influenza virus which is the most likely to cause epidemic or pandemic infections among all other types is further categorized into many subtypes depending on the type of certain viral proteins. Viruses of the influenza A type which are able to cross-infect and recombine between different species are the most virulent human pathogens. Several severe influenza pandemics were caused by this influenza virus type like for example by the subtypes H1N1 (1918, 2009), H3N2 (1968) or H5N1 (2004).

Therefore, early treatment of influenza is vital. Conventional therapies for treatment of influenza include administration of antiviral drugs like neuraminidase inhibitors (oseltamivir and zanamivir) and M2 protein inhibitors (adamantane derivatives) or viral polymerase inhibitors like ribavirin, all of them are associated with more or less severe adverse events and several contraindications or interactions with further drugs need to be considered while the therapeutic benefit might be limited due to a high risk of drug resistance. Moreover, toxicity studies indicated a possible tumorigenic and embryo toxic potential of neuraminidase inhibitors.

Thus, there is a strong need for therapeutically effective compounds and improved ways for successfully treating influenza, especially infections caused by influenza type A. As usual, it is generally desirable to have compounds with reduced risk for side effects, which can be prepared in a cost-effective way.

Recently, Traditional Chinese medicine as well as complementary and alternative medicine has getting popular providing a lot of treatment options. Traditional Chinese medicines based on plant materials as well as plants or respective components gained from plants usually allow for treatment of various diseases and conditions while bearing a reduced risk for side effects. In view of the rich medicinal plant resources, available respective medicines can usually be produced in a cost-effective way. Accordingly, there has been a lot of research with regard to plants and respective ingredients for treatment of several diseases and conditions.

For example, *Baphicacanthus cusia* (Nees) Bremek is distributed in Southern China and already used as a traditional Chinese medicine named Nan-Ban-Lan-Gen (NBLG) (Ho Y. L. et al., Am. J. Chin. Med. 2003, 31, 61). The nature and taste of this material is cold and bitter, and it is commonly used for treating conditions associated with heat and toxins. It was recorded in the People's Republic of China Pharmacopoeia (2015) as a Chinese herbal medicine for anti-viral treatment and has also been listed as one of the major anti-severe acute respiratory syndrome (SARS) medicines during the outbreak of SARS in 2003.

Till now indigoid indole alkaloids, quinazolinone alkaloids, monoterpenes, triterpenes, flavonoids, sterols, anthraquinones, benzoxazinones, and lignans have been reported to be present in *Baphicacanthus cusia* (Gu W. et al., J. Nat. Prod. 2014, 77, 2590). The specific structure of the ingredients in *Baphicacanthus cusia* is not completely known and the number of reports dealing with an isolation of ingredients from *Baphicacanthus cusia* let alone a successful isolation of those ingredients is limited. Since diversified components in Chinese herbal medicines often act via multiple modes, there is a strong need for identifying and providing components in isolated form with sufficient therapeutic efficiency, in particular with sufficient anti-viral activity such as for treatment of influenza like influenza type A infections caused by H1N1. Having those active ingredients in isolated form could further reduce the risk of side effects or interactions which might limit the therapeutic use due to the presence of further ingredients with reduced or insufficient efficacy for treating the respective disease.

SUMMARY OF THE INVENTION

The invention provides in a first aspect a method of isolating at least one ingredient selected from the group consisting of an alkaloid, a triterpenoid, a lignan, a phenylethanoid, a sesquiterpene lactone and a flavonoid from *Baphicacanthus cusia* which method comprises steps of:
  (i) subjecting *Baphicacanthus cusia* plant material to a solvent extraction with an extraction solvent for obtaining a crude extract, wherein the extraction solvent comprises an aliphatic alcohol and wherein the solvent extraction is carried out at temperatures above 40° C. and wherein the *Baphicacanthus cusia* plant material comprises roots;
  (ii) contacting the crude extract with at least a first, a second and a third separation solvent for obtaining at least a first, a second and a third layer, wherein the first separation solvent comprises water, the second separation solvent comprises an ester and the third separation solvent comprises an aliphatic alcohol, and wherein the obtained first layer comprises the first separation solvent, the second layer comprises the second separation solvent and the third layer comprises the third separation solvent;
  (iii) subjecting at least one of the second or the third layer to at least a first and a second chromatographic separation step. In particular, the first and the second chromatographic separation step are carried out with liquid column chromatography including separating by means of fragmentation.

The ingredient isolated from *Baphicacanthus cusia* is usually an active ingredient in particular an ingredient which at least contributes to the therapeutic effects of *Baphicacanthus cusia*, in particular it is an ingredient which possesses anti-viral efficacy. The ingredient is in particular selected from the group consisting of a benzoheterocyclic alkaloid, a quinoline alkaloid, an indole alkaloid, a triterpenoid, a lignan and a phenylethanoid and is preferably selected from the group consisting of:

a compound of Formula (1)

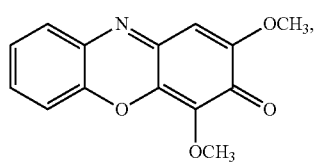

Formula (1)

a compound of Formula (2)

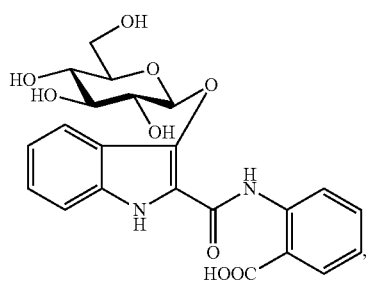

Formula (2)

a compound of Formula (5)

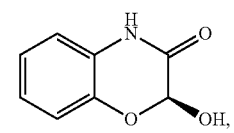

Formula (5)

a compound of Formula (6)

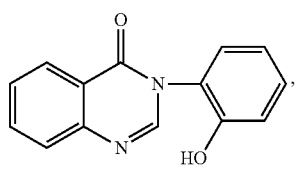

Formula (6)

a compound of Formula (7)

Formula (7)

a compound of Formula (8)

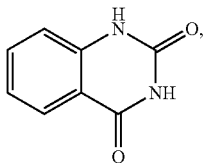

Formula (8)

a compound of Formula (9)

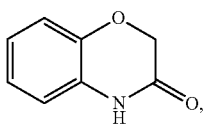

Formula (9)

a compound of Formula (11)

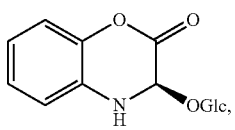

Formula (11)

a compound of Formula (14)

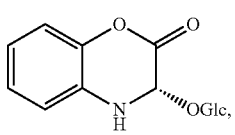

Formula (14)

a compound of Formula (19)

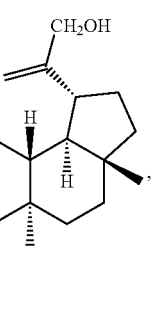

Formula (19)

a compound of Formula (20)

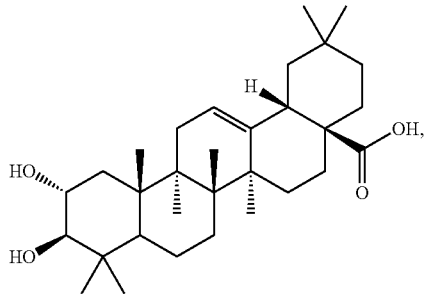

Formula (20)

a compound of Formula (21)

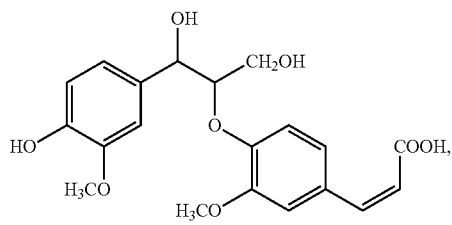

Formula (21)

a compound of Formula (25)

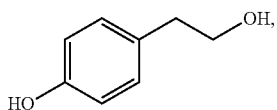

Formula (25)

and
a compound of Formula (26)

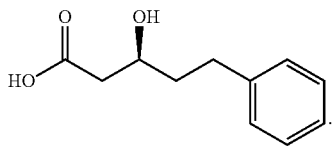

Formula (26)

The present invention also refers to a compound having Formula (1)

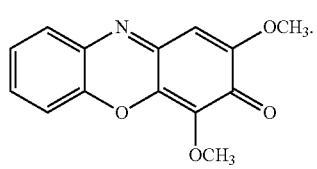

Formula (1)

and a compound having Formula (2)

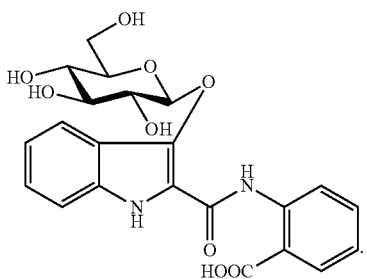

Formula (2)

In another aspect, the present invention refers to a composition, in particular a pharmaceutical composition, comprising and in particular essentially consisting of:
- at least one, in particular one ingredient, in particular as pharmaceutically effective ingredient, isolated from *Baphicacanthus cusia* according to the method described above, and
- at least one pharmaceutically tolerable excipient such as one or more of a diluent, a filler, a binder, a disintegrant, a lubricant, a coloring agent, a surfactant and a preservative.

The ingredient comprised in the composition is in particular selected from the group consisting of:
a compound of Formula (1)

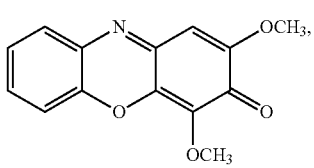

Formula (1)

a compound of Formula (2)

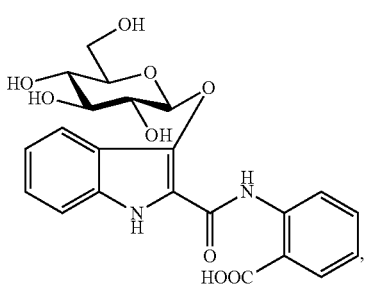

Formula (2)

a compound of Formula (5)

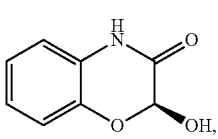

Formula (5)

a compound of Formula (7)

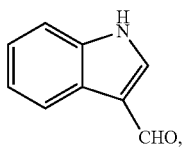

Formula (7)

a compound of Formula (9)

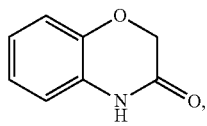

Formula (9)

and
a compound of Formula (19)

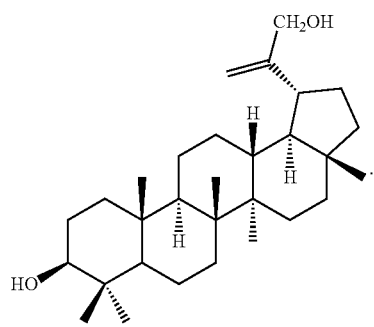

Formula (19)

Further in accordance with the present invention is a method of treating a subject suffering from a viral disease, in particular caused by Influenza A virus subtype H1N1, comprising administering an effective amount of at least one ingredient isolated from *Baphicacanthus cusia* according to the method described above to the subject.

In particular, the method comprises administering an affective amount of an ingredient selected from:
a compound of Formula (5)

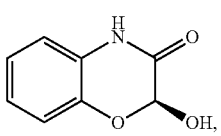

Formula (5)

a compound of Formula (7)

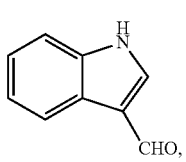

Formula (7)

a compound of Formula (9)

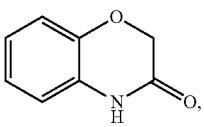

Formula (9)

or or a compound of Formula (19)

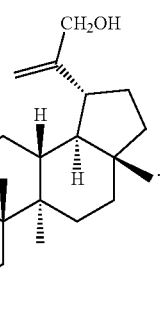

Formula (19)

In still a further aspect, the present invention refers to a method of treating a subject suffering from a viral disease, in particular caused by Influenza A virus subtype H1N1, comprising administering an effective amount of a compound having one of the following Formulas to the subject:

Formula (5)

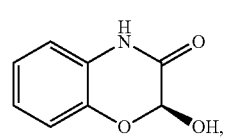

Formula (5)

Formula (7)

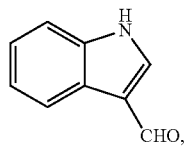

Formula (7)

Formula (9)

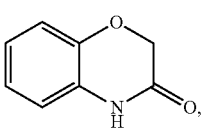

Formula (9)

or
Formula (19)

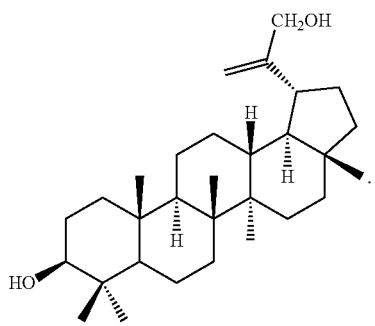

Formula (19)

The method of the present invention of isolating at least one ingredient from *Baphicacanthus cusia* can be used to isolate and obtain for example about 30 ingredients. Among them are the new alkaloids baphicacanthin A (compound of Formula (1)) and baphicacanthin B (compound of Formula (2)) which have not been previously reported.

Moreover, the method of the present invention allows for further isolating 12 compounds which could not or have not been isolated so far, i.e. which can be isolated for the first time with the method of the present invention, namely 2-hydroxy-1,4-benzoxazin-3-one (compound of Formula (5)), 3-(2'-hydroxyphenyl)-4(3H)-quinazolinone (compound of Formula (6)), 1H-indole-3-carbaldehyde (compound of Formula (7)), benzouracil (compound of Formula (8)), 2H-1,4-benzoxazin-3-one (compound of Formula (9)), acanthaminoside (compound of Formula (11)), acanthaminoside isomer (compound of Formula (14)), lup-20(29)-en-3β, 30-diol (compound of Formula (19)), maslinic acid (compound of Formula (20)), guaiacylglycerol-β-ferulic acid ether (compound of Formula (21)), tyrosol (compound of Formula (25)), β-hydroxy-benzenepentanoic acid (compound of Formula (26)).

Other features and aspects of the invention will become apparent by consideration of the following detailed description and accompanying drawings.

DESCRIPTION OF THE EMBODIMENTS

Figure 1:
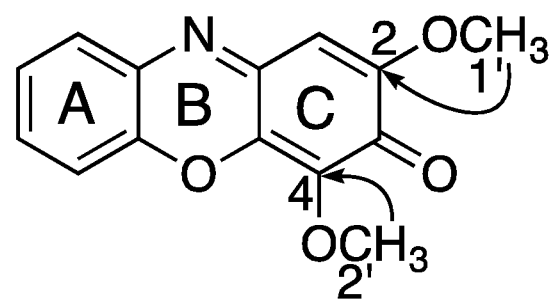
FIG. 1 shows selected HMBC correlations of baphicacanthin A (compound of Formula (1).

The following preparations and examples are given to enable those skilled in the art to more clearly understand and to practice the present invention. They should not be considered as limiting the scope of the invention, but merely as being illustrative and for representing preferred embodiments thereof. The technical terms used in the present patent application have the meaning as commonly understood by a respective skilled person unless specifically defined otherwise.

As used herein and in the claims, "comprising" means including the following elements but not excluding others. "Essentially consisting of" means that the material consists of the respective element along with usually and unavoidable impurities such as side products and components usually resulting from the respective preparation or method for obtaining the material such as traces of further components. "Consisting of" means that the material is solely consist of, i.e. is formed by the respective element. In a first aspect, the invention provides a method of isolating and preferably purifying at least one ingredient from Baphicacanthus cusia, usually an active ingredient in particular with anti-viral efficacy. The ingredient is selected from the group consisting of an alkaloid, a triterpenoid, a lignan, a phenylethanoid, a sesquiterpene lactone and a flavonoid. The method of the present invention comprises steps of:

(i) subjecting *Baphicacanthus cusia* plant material to solvent extraction with an extraction solvent for obtaining a crude extract, wherein the extraction solvent comprises an aliphatic alcohol and wherein the solvent extraction is carried out at temperatures above 40° C. and wherein the *Baphicacanthus cusia* plant material comprises roots;

(ii) contacting the crude extract with at least a first, a second and a third separation solvent for obtaining at least a first, a second and a third layer, wherein the first separation solvent comprises water, the second separation solvent comprises an ester and the third separation solvent comprises an aliphatic alcohol, and wherein the obtained first layer comprises the first separation solvent, the second layer comprises the second separation solvent and the third layer comprises the third separation solvent;

(iii) subjecting at least one of the second or the third layer to at least a first and a second chromatographic separation step. Preferably the first and the second chromatographic separation step are carried out with liquid column chromatography including separating by means of fragmentation.

Optionally, the method includes further steps after step (iii) of purifying the at least one ingredient.

The term "isolating" or "isolation" used herein means separating a combination of two or more or one single ingredient from components present in the *Baphicacanthus cusia* plant material. In particular, the method is for isolating a combination of at most 10, further preferred at most 5, still further preferred at most two and in particular one single ingredient, usually an active ingredient in particular with anti-viral efficacy, from Baphicacanthus cusia plant material.

The term "purifying" as used herein refers to methods generally known to the skilled person for purifying compounds like evaporation, lyophilization or (re-)crystallization for obtaining a desired degree of purity, i.e. a desired degree of absence of impurities. Preferably, the at least one ingredient isolated from *Baphicacanthus cusia* is selected from the group consisting of a benzoheterocyclic alkaloid, a quinoline alkaloid, an indole alkaloid, a triterpenoid, a lignan, and a phenylethanoid. More preferably, the at least one ingredient isolated from *Baphicacanthus cusia* is selected from the group consisting of a benzoheterocyclic alkaloid, an indole alkaloid and a triterpenoid.

"Alkaloids" are known to the skilled person as a class of components present in various plants characterized by a chemical structure with at least one nitrogen atom, usually at least one heterocyclic nitrogen atom. Alkaloids can be divided into several subgroups depending on the specific nitrogen containing heterocyclic ring system such as indole alkaloids based on an indole ring as structural component or quinoline alkaloids based on a quinoline ring structure like a quinolinone or a quinazolinone as structural component. Preferably, the alkaloid according to the present invention is of one of the subgroups selected from a quinoline alkaloid, an indole alkaloid or a benzoheterocyclic alkaloid. Benzoheterocyclic alkaloids referred to herein comprise a heterocyclic ring with a nitrogen atom usually based on a morpholine or pyrimidine ring fused to a benzene ring.

Preferably, the benzoheterocyclic alkaloid is selected from a compound:

having Formula (1), which is named herein baphicacanthin A:

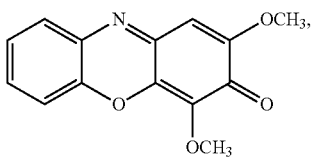

Formula (1)

having Formula (3), which is known as 2-benzoxazolinone:

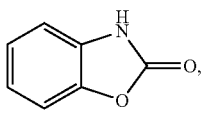

Formula (3)

having Formula (5), which is known as 2-hydroxy-1,4-benzoxazin-3-one:

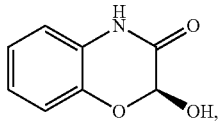

Formula (5)

having Formula (8), which is known as benzouracil:

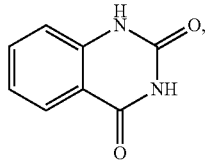

Formula (8)

having Formula (9), which is known as 2H-1,4-benzoxazin-3-one:

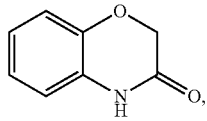

Formula (9)

having Formula (11), which is known as acanthaminoside:

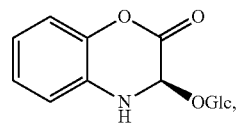

Formula (11)

or a compound having Formula (14), which is known as acanthaminoside isomer:

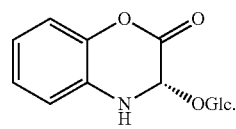

Formula (14)

Preferably, the quinoline alkaloid is selected from a compound:

having Formula (4), which is known as tryptanthrin:

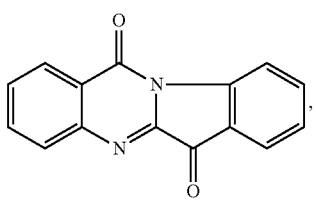

Formula (4)

having Formula (6), which is known as 3-(2'-hydroxyphenyl)-4(3H)-quinazolinone:

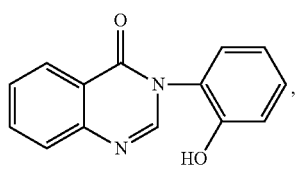

Formula (6)

having Formula (12), which is known as 4(3H)-quinazolinone:

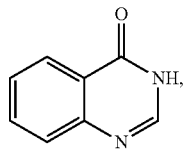

Formula (12)

or a compound having Formula (13), which is known as deoxyvasicinone:

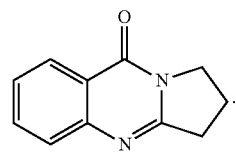

Formula (13)

Preferably, the indole alkaloid is selected from a compound:

having Formula (2), which is named herein baphicacanthin B:

Formula (2)

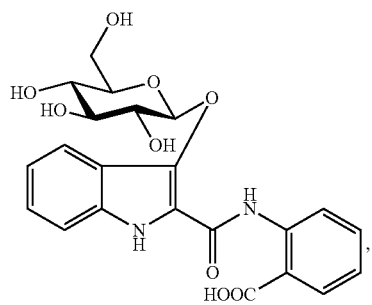

having Formula (7), which is known as 1H-indole-3-carbaldehyde:

Formula (7)

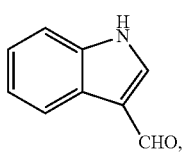

or a compound having Formula (10), which is known as 3-carboxyindole:

Formula (10)

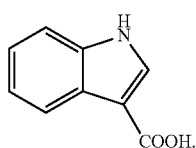

"Triterpenoids" are known to the skilled person as components in plants based on or derived from a cyclization of the 30 carbon atom containing hydrocarbon squalene usually leading to tetracyclic and pentacyclic ring systems. Preferably, the triterpene of the present invention is selected from a compound:

having Formula (15) known as lupeol:

Formula (15)

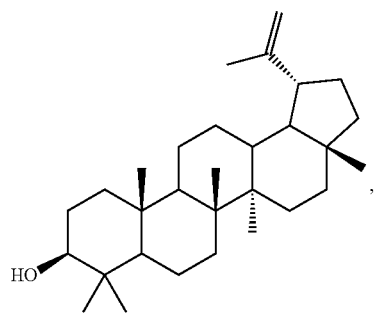

having Formula (16) known as betulin:

Formula (16)

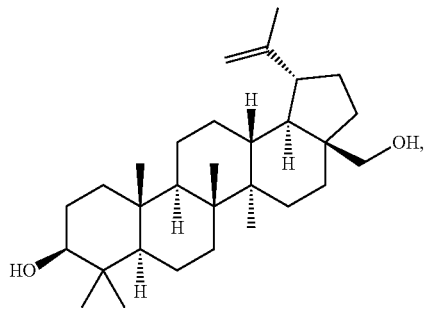

having Formula (17) known as betulinic acid:

Formula (17)

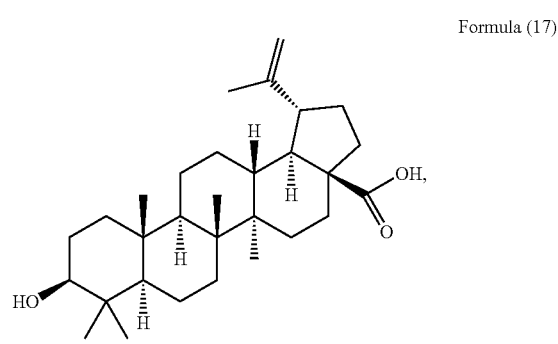

having Formula (18) known as ursolic acid:

Formula (18)

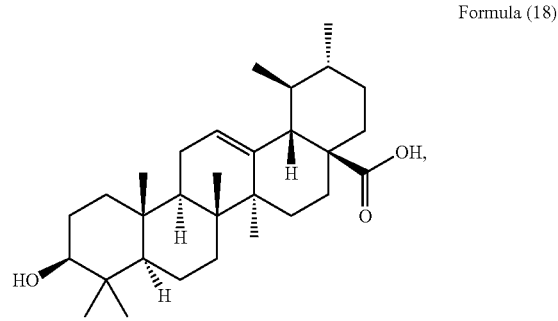

having Formula (19) known as lup-20(29)-en-3β, 30-diol:

Formula (19)

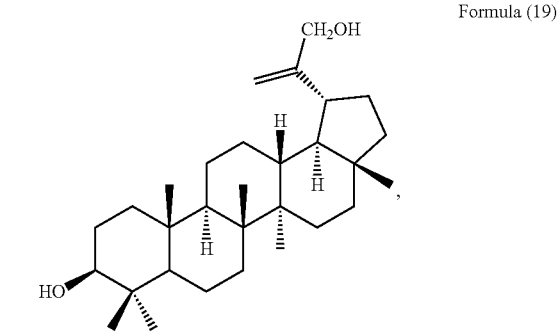

or a compound having Formula (20) known as maslinic acid:

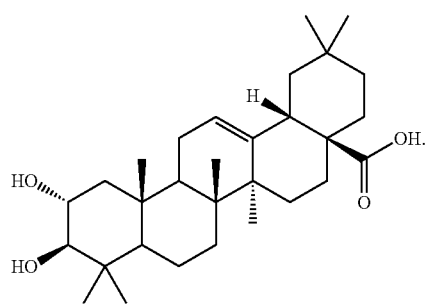

Lignans are a class of compounds having two phenyl propane moieties usually coupled at the central carbon atom in the side chain, i.e. they represent dimeric phenyl propanoids and are present in various plants. Lignans according to the present invention in particular are selected from a compound:

having Formula (21) known as guaiacylglycerol-β-ferulic acid ether:

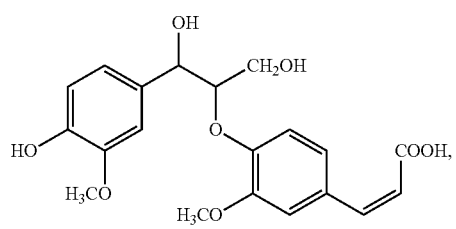

having Formula (22) known as (2S, 3R, 4S)-lyoniresinol-3α-O-β-D-glucopyranoside:

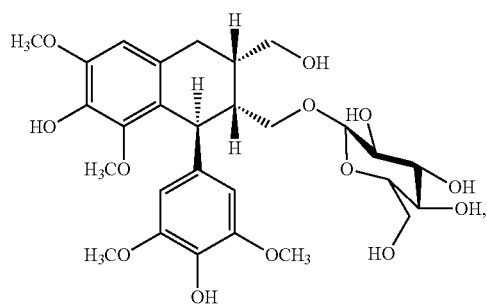

having Formula (23) known as (2R, 3S, 4R)-lyoniresinol-3α-O-β-D-glucopyranoside:

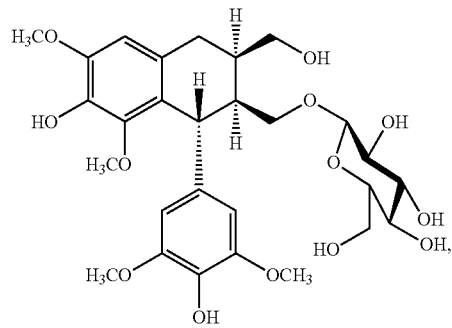

or a compound having Formula (24) known as (+)-5,5'-dimethoxy-9-O-β-D-glucopyranosyl secoisolariciresinol:

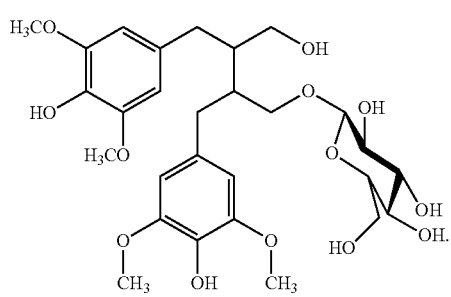

Phenylethanoids are phenolic compounds characterized by a phenethyl alcohol structure and are in particular selected from a compound:

having Formula (25) known as tyrosol:

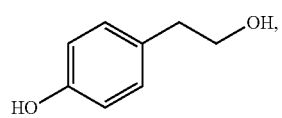

having Formula (26) known as β-hydroxy-benzenepentanoic acid:

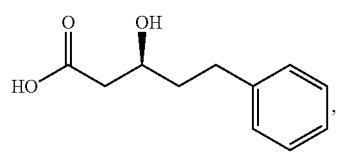

having Formula (27) known as acteoside:

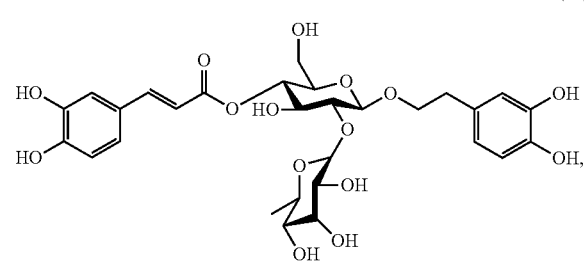

or a compound having Formula (28) known as acteoside isomer:

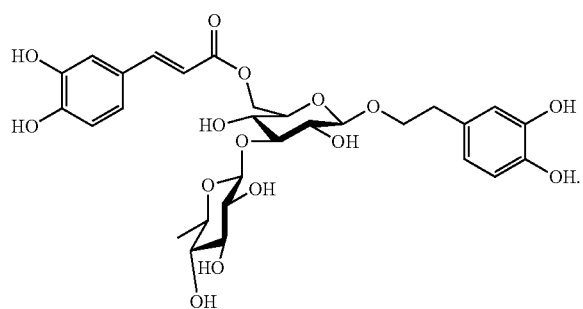

Sesquiterpenes are known to be based on a structural component with 15 carbon atoms, namely three isoprene units and usually have a mono- or bicyclic structure, wherein sesquiterpene lactones are sesquiterpenes containing a lactone structure. Sesquiterpene lactones of the present invention preferably refer to a compound having Formula (29) also known as loliolide:

Formula (29)

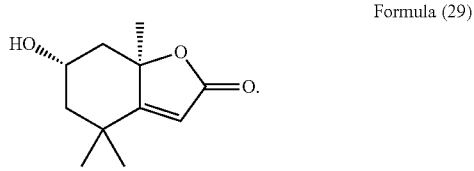

Flavonoids as known to the skilled person are phenolic compounds present in various plants comprising two aromatic rings linked via a three carbon atom containing group. Flavonoids in particular include the compound of Formula (30), which is of the flavone type and known as hispiduloside:

Formula (30)

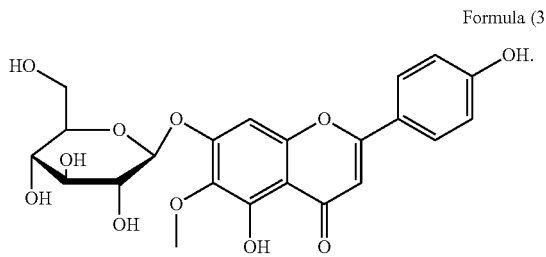

In particular, the method of the present invention allows for the isolation and preferably purification of at least one of the following ingredients, i.e. at least one of the following ingredients is preferably isolated and preferably purified:
 compound of Formula (1), i.e. baphicacanthin A,
 compound of Formula (2), i.e. baphicacanthin B,
 compound of Formula (5), i.e. 2-hydroxy-1,4-benzoxazin-3-one,
 compound of Formula (6), i.e. 3-(2'-hydroxyphenyl)-4(3H)-quinazolinone,
 compound of Formula (7), i.e. 1H-indole-3-carbaldehyde,
 compound of Formula (8), i.e. benzouracil,
 compound of Formula (9), i.e. 2H-1,4-benzoxazin-3-one,
 compound of Formula (11), i.e. acanthaminoside,
 compound of Formula (14), i.e. acanthaminoside isomer,
 compound of Formula (19), i.e. lup-20(29)-en-3β, 30-diol,
 compound of Formula (20), i.e. maslinic acid,
 compound of Formula (21), i.e. guaiacylglycerol-β-ferulic acid ether,
 compound of Formula (25), i.e. tyrosol, and/or
 compound of Formula (26), i.e. β-hydroxy-benzenepentanoic acid.

In more preferred embodiments of the present invention, the method of the present invention allows for the isolation and preferably purification of at least one of the following ingredients, i.e. at least one of the following ingredients is more preferably isolated and preferably purified, in particular one of the following ingredients:
 compound of Formula (1), i.e. baphicacanthin A,
 compound of Formula (2), i.e. baphicacanthin B,
 compound of Formula (5), i.e. 2-hydroxy-1,4-benzoxazin-3-one,
 compound of Formula (7), i.e. 1H-indole-3-carbaldehyde,
 compound of Formula (9), i.e. 2H-1,4-benzoxazin-3-one, and/or
 compound of Formula (19), i.e. lup-20(29)-en-3β, 30-diol.

In most preferred embodiments of the present invention, the method of the present invention allows for the isolation and preferably purification of one of the following ingredients, i.e. one of the following ingredients is most preferably isolated and preferably purified with the method of the present invention:
 compound of Formula (5), i.e. 2-hydroxy-1,4-benzoxazin-3-one,
 compound of Formula (7), i.e. 1H-indole-3-carbaldehyde,
 compound of Formula (9), i.e. 2H-1,4-benzoxazin-3-one, or
 compound of Formula (19), i.e. lup-20(29)-en-3β, 30-diol.

In especially preferred embodiments, one of the compounds of Formula (7), i.e. 1H-indole-3-carbaldehyde, or of Formula (19), i.e. lup-20(29)-en-3β, 30-diol, is isolated and preferably purified with the method of the present invention.

The *Baphicacanthus cusia* plant material comprises and in particular essentially consists of roots of *Baphicacanthus cusia*. The method of the present invention preferably further comprises steps before carrying out step (i) of
 a) drying the *Baphicacanthus cusia* plant material, and/or
 b) cutting, shredding, milling and/or pulverizing the *Baphicacanthus cusia* plant material.

In particular both of steps a) and b) are carried out before step (i).

Hence, the *Baphicacanthus cusia* plant material is preferably dried before step (i), in particular before cutting, shredding, milling and/or pulverizing it. Drying is usually carried out with air at room temperature, i.e. at 25+/−2° C., or alternatively at temperatures of 50-100° C. for 0.5-1 h or with desiccants or a desiccator. Preferably, step b) includes cutting the *Baphicacanthus cusia* plant material. In most preferred embodiments of the present invention, the *Baphicacanthus cusia* plant material comprises, in particular essentially consists of air-dried and subsequently cut roots of *Baphicacanthus cusia*.

For example, about 1 kg to 5 kg of the *Baphicacanthus cusia* plant material, in particular about 3 kg, can be used in the method of the present invention. In particular, the amount of *Baphicacanthus cusia* plant material in relation to the total amount of the extraction solvent used in step (i) is preferably between 10 mg/ml and 200 mg/ml, further preferred between 20 mg/ml and 150 mg/ml, in particular between 30 mg/ml and 50 mg/ml such as 35 mg/ml to 45 mg/ml and most preferably about 41.66 mg/ml plant material relative to the total amount of extraction solvent used for extracting the *Baphicacanthus cusia* plant material in step (i). In embodiments, in which the solvent extraction in step (i) is carried out three times, each solvent extraction is preferably carried out such that the amount of *Baphicacanthus cusia* plant material in relation to the amount of the extraction solvent used in each step is 100 mg/ml to 167 mg/ml such as 100 mg/ml in the first solvent extraction, 125 mg/ml in the second and 167 mg/ml in the third, wherein the amount of extraction solvent in the second and third solvent extraction is calculated in relation to the starting weight of the *Baphicacanthus cusia* plant material used in the first solvent extraction.

The extraction solvent comprises an aliphatic alcohol, which means herein an aliphatic hydrocarbon, preferably a branched or straight chain alkane, wherein at least one hydrogen atom of the aliphatic hydrocarbon is substituted with a hydroxyl group, preferably one hydrogen atom is substituted with a hydroxyl group referenced as monohydric aliphatic alcohol. More preferably, the aliphatic alcohol of the extracting solvent is a monohydric aliphatic alcohol, still more preferably a monohydric alcohol with 1 to 4 carbon atoms, further preferably with 2 to 3 carbon atoms. I.e. the aliphatic alcohol of the extracting solvent is more preferably selected from methanol, ethanol, propanol, isopropanol, n-butanol, isobutanol, sec-butyl alcohol, tert-butyl alcohol or mixtures thereof and further preferably from ethanol, propanol, isopropanol or mixtures thereof. Most preferably, the aliphatic alcohol of the extraction solvent is ethanol. The extraction solvent preferably further comprises water and more preferably essentially consists of the aliphatic alcohol and water, in particular of ethanol and water.

Most preferably, the extraction solvent is aqueous ethanol, in particular above 70 vol. % to below 90 vol. %, preferably 75 vol. % to 85 vol. %, in particular about 80 vol. % aqueous ethanol. At least 10 L of extraction solvent, in particular aqueous ethanol, may be used in step (i).

The solvent extraction is preferably carried out for 0.5 to 8.0 h, more preferably 1.5 to 6 h and most preferably about 3 h. In embodiments, in which the solvent extraction in step (i) is carried out at least two times and in particular for three times, each solvent extraction is preferably carried out for 0.5 to 2 h, preferably 1 h. The temperatures are preferably above 45° C., in particular at least 50° C., and most preferably the *Baphicacanthus cusia* plant material is refluxed with the extraction solvent.

The solvent extraction in step (i) is preferably carried out at least two, more preferably at least three times and in particular three times. In such embodiments, the extracts are subsequently combined for forming the crude extract. Thus, in especially preferred embodiments, the *Baphicacanthus cusia* plant material is refluxed with the extraction solvent, in particular aqueous ethanol like about 80 vol. % aqueous ethanol at least 2 times, in particular three times. I.e. the extraction of step (i) is preferably carried out three times with the *Baphicacanthus cusia* plant material. For example, the *Baphicacanthus cusia* plant material can be subsequently extracted with about 30 L, about 24 L and about 18 L, respectively, of aqueous ethanol like about 80 vol. % aqueous ethanol.

Contacting the crude extract with the separation solvents in step (ii) preferably means adding in particular accompanied by shaking the at least first, second and third separation solvent to the crude extract which is in particular carried out sequentially. In preferred embodiments of the present invention, the crude extract is added, preferably suspended, in the first separation solvent, then the second separation solvent is added preferably accompanied by shaking for forming the first and the second layer and the second layer is then separated from the first layer. Subsequently, the third separation solvent is added to the first layer preferably accompanied by shaking for forming the third layer. The term "layers" used herein and as generally understood by the skilled person means separated phases resulting from contacting at least two solvents which are in particular substantially immiscible or immiscible with each other, in the present invention for example the first and the second separation solvent and the first and the third separation solvent.

For example, 1 L of the second and 1 L of the third separation solvent may be used for contacting the crude extract.

The first separation solvent preferably essentially consists of water. The second separation solvent comprises an ester, in particular a $C_1$-$C_6$ aliphatic alcohol ester of a $C_1$-$C_7$ alkyl carboxylic acid. Further preferably, the ester is a $C_3$-$C_7$ ester, in particular ethyl acetate or ethyl formate. In most preferred embodiments of the present invention, the second separation solvent comprises and preferably essentially consists of ethyl acetate. The third separation solvent comprises an aliphatic alcohol, preferably a monohydric aliphatic alcohol. More preferably, the aliphatic alcohol of the third separation solvent is a monohydric aliphatic alcohol having 3 to 5 carbon atoms, preferably an alkane with 3 to 5 carbon atoms with one hydrogen atom being replaced with a hydroxyl group. I.e. the aliphatic alcohol of the third separation solvent is more preferably selected from propanol, isopropanol, n-butanol, isobutanol, sec-butyl alcohol or tert-butyl alcohol pentan-1-ol or a pentanol isomer like pentan-2-ol, pentan-3-ol, 2-methylbutan-1-ol and the like. More preferably, the aliphatic alcohol of the third separation solvent is n-butanol and most preferably the third separation solvent comprises and preferably essentially consists of n-butanol.

The method of the present invention further comprises a step (iii) of subjecting the second layer and/or the third layer to at least the first and the second chromatographic separation step. In particular, the first and the second chromatographic separation step are carried out with liquid chromatography including column chromatography like classical (low pressure) column chromatography usually operating with a low pressure up to about 0.5 MPa, medium pressure liquid chromatography (MPLC) which usually operates at higher pressures, high-performance liquid chromatography (HPLC) usually with operational pressures up to 5 MPa or higher or thin layer chromatography (TLC). MOPLC is preferably carried out as preparative MPLC and HPLC is preferably carried out as semi-preparative or preparative HPLC. Preferably, the first and the second chromatographic separation step are selected from traditional (low pressure) column chromatography, medium pressure liquid chromatography (MPLC) or high-performance liquid chromatography (HPLC). Preferably, either the second or the third layer is subjected to the at least first and second chromatographic separation step.

The first chromatographic separation step is in particular selected from classical (low pressure) column chromatography for example with a silica gel as stationary phase or a styrene-divinylbenzene polymer resin. The preferred conditions depend on the fact whether the second or the third layer is subjected to the first chromatographic separation step and will be further referenced below.

The second chromatographic separation step may comprise one of liquid chromatography, which may be carried out as classical column chromatography, MPLC or HPLC.

The stationary phase is preferably selected from silica gel or a reverse phase, in particular a C18 reverse phase. Classical column chromatography as second chromatographic separation step is preferably carried out with silica gel with a mesh grade of preferably 60 to 400, more preferably 200 to 300 mesh and preferably a pore size of about 60 Å, in particular with silica gel 60 as commercially available. Alternatively, a reverse phase can be used, namely a stationary phase having alkyl chains covalently bonded to a solid support leading to a hydrophobic stationary phase. The reverse phase in particular includes C18 phases like RP-18, i.e. with octadecyl-chains (C18 chains) in particular with a particle size of 40 µm to 60 µm such as about 45 µm.

MPLC as second chromatographic separation step is in particular carried out with a reverse phase as stationary phase, in particular a C18 reverse phase like RP-18, i.e. with octadecyl-chains (C18 chains), in particular with a particle size of 40 µm to 63 µm and preferably with column dimensions of about 36×460 mm.

HPLC as second chromatographic separation step is preferably carried out with a reverse phase as stationary phase, in particular a C18 reverse phase with a particle size of 3 µm to 10 µm like 5 µm or 10 µm and preferably with column dimensions of 250×10 mm or 250×22 mm.

In one embodiment of the present invention, the second layer is subjected to the at least first and second chromatographic separation step, in particular in order to isolate and preferably purify one or more of the following ingredients:

a compound of Formula (1), i.e. baphicacanthin A,
a compound of Formula (3), i.e. 2-benzoxazolinone,
a compound of Formula (4), i.e. tryptanthrin,
a compound of Formula (5), i.e. 2-hydroxy-1,4-benzoxazin-3-one,
a compound of Formula (6), i.e. 3-(2'-hydroxyphenyl)-4 (3H)-quinazolinone,
a compound of Formula (7), i.e. 1H-indole-3-carbaldehyde,
a compound of Formula (8), i.e. benzouracil,
a compound of Formula (9), i.e. 2H-1,4-benzoxazin-3-one,
a compound of Formula (10), i.e. 3-carboxyindole,
a compound of Formula (11), i.e. acanthaminoside,
a compound of Formula (12), i.e. 4(3H)-quinazolinone,
a compound of Formula (13), i.e. deoxyvasicinone,
a compound of Formula (15), i.e. lupeol,
a compound of Formula (16), i.e. betulin,
a compound of Formula (17), i.e. betulinic acid,
a compound of Formula (18), i.e. ursolic acid.
a compound of Formula (19), i.e. lup-20(29)-en-3β, 30-diol,
a compound of Formula (20), i.e. maslinic acid,
a compound of Formula (25), i.e. tyrosol,
a compound of Formula (27), i.e. acteoside,
a compound of Formula (28), i.e. acteoside isomer,
a compound of Formula (29), i.e. loliolide, and/or
a compound of Formula (30), i.e. hispiduloside.

In embodiments of the present invention, in which the second layer is subjected to the at least first and second chromatographic separation step, the first chromatographic separation step is preferably carried out by means of liquid column chromatography in particular by means of a classical column chromatography. The first chromatographic separation step preferably includes fractionating the second layer and its components, respectively, to obtain several fractions, in particular at least 10 fractions, more preferably at least 13 fractions, i.e. including collecting and selecting individual eluate fractions rich in the at least one ingredient to be isolated. The liquid column chromatography as first chromatographic separation step is preferably carried out with silica gel as stationary phase, in particular with a mesh grade of 60 to 400, more preferably of 200 to 300 mesh. The pore size of the silica gel is preferably about 60 Å. In especially preferred embodiments of the present invention, silica gel 60 as commercially available is used as stationary phase in the first chromatographic separation step. The column dimensions are, for example, 35×5 cm.

The first chromatographic separation step by means of liquid column chromatography is in embodiments, in which the second layer is subjected to the at least first and second chromatographic separation step, preferably carried out as gradient elution, i.e. with a gradient of at least two, preferably two eluting solvents. More preferably, the eluting solvents comprise an ester and hydrocarbons. Preferably, the first eluting solvent comprises an ester, in particular a $C_3$-$C_7$ ester, most preferably ethyl acetate. The second eluting solvent preferably comprises hydrocarbons in particular $C_5$ and $C_6$ hydrocarbons, most preferably petroleum ether. In especially preferred embodiments of the present invention, the first eluting solvent comprises and preferably essentially consists of ethyl acetate and the second eluting solvent comprises and preferably essentially consists of petroleum ether. The gradient of the first eluting solvent to the second eluting solvent applied is preferably 9:1 to 5:5, in particular according to table 1.

TABLE 1

| preferred gradient in the first chromatographic separation step of the second layer Gradient first to second eluting solvent |
| --- |
| 9:1 |
| 8:2 |
| 7:3 |
| 6:4 |
| 5:5 |

Preferably, fractions are collected by volume such as for example 100 ml of each fraction (also referenced as "collected fractions"). From the collected fractions, at least 10 fractions, more preferably 10 to 15 fractions are selected ("selected fractions") and in particular 13 fractions are selected further referenced as "selected fraction no. 1" to "selected fraction no. 13".

The selected fractions are preferably selected based on a thin layer chromatography (TLC) monitoring from the collected fractions which is usual practice in the art, i.e. the chemical composition of each collected fraction is visualized by using TLC. Those collected fractions with similar chemical compositions are combined such that preferably about 13 selected fractions are obtained. More specifically, fractions with certain volume each are preferably collected and then collected fractions with a similar chemical composition are each combined for forming selected fractions. As a non-limiting and illustrative example, 100 collected fractions with 100 ml/each may be collected, then collected fractions 1 to 10 may be combined to yield selected fraction no. 1, collected fractions 10-15 may be combined to yield selected fraction no. 2, collected fractions 15-25 may be combined to yield selected fraction no. 3, and so on, based on TLC results.

Most preferably, about 13 selected fractions are obtained from the collected fractions based on their TLC results. TLC is preferably carried out with silica coated plates, in particular with silica gel 60 $_{F254}$. For example, TLC plates can be used having a thickness of about 0.2 mm. The presence of ingredients selected from alkaloids, triterpenoids, lignans, phenylethanoids, sesquiterpene lactones and flavonoids can for example be verified with usual and well-known reagents, under UV light of, for example, 254 and/or 366 nm and/or with respective standards. Non limiting examples of suitable reagents include, for example, sulfuric acid, aluminium chloride, p-anisaldehyde-sulfuric acid, antimony (III) chloride, ethanolamine diphenylborate, phosphoric acid, tin (IV) chloride.

In embodiments of the present invention, in which the second layer is subjected to the at least first and second chromatographic separation step, the second chromatographic separation step may be carried out with liquid chromatography such as classical column chromatography, MPLC or HPLC. The stationary phase is preferably selected from silica gel or a reverse phase, in particular a C18 reverse phase. Classical column chromatography as second chromatographic separation step in embodiments in which the second layer is subjected to the chromatographic separation steps is preferably carried out with silica gel with a mesh grade of preferably 200 to 300 mesh and preferably a pore size of about 60 Å, in particular with silica gel 60 as commercially available. Alternatively, a C18 reverse phase like RP-18 and in particular with a particle size of about 45 µm is used. MPLC as second chromatographic separation step is in particular carried out with a C18 reverse phase like RP-18 in particular with a particle size of 40 µm to 63 µm and preferably with column dimensions of about 36×460 mm. HPLC as second chromatographic separation step is preferably carried out with a C18 reverse phase with a particle size of 3 µm to 10 µm like 5 µm or 10 µm and preferably with column dimensions of 250×10 mm or 250×22 mm.

The specific preferred conditions for carrying out the second chromatographic separation step depend on the ingredients to be isolated and are further referenced below.

For isolating the compound of Formula (15), selected fraction no. 3 is preferably subjected to a classical column chromatography with silica gel and with eluting solvents comprising a $C_4$ to $C_8$ straight chain hydrocarbon and a $C_3$ to $C_7$ ester, most preferably with n-hexane-ethyl acetate and a gradient of 9:1 to 5:5.

For isolating one or more of the compounds of Formula (3), (4) and/or (16), selected fraction no. 4 is preferably subjected to a classical column chromatography with a C18 reverse phase with eluting solvents comprising water and an aliphatic $C_1$ to $C_3$ alcohol, in particular with methanol-water with a gradient of 9:1 to 7:3 and subsequently to a classical column chromatography with silica gel and eluting solvents comprising a $C_4$ to $C_8$ straight chain hydrocarbon and a $C_3$ to $C_7$ ester, in particular with n-hexane-ethyl acetate and a gradient of 9:1 to 6:4.

For isolating one or more of the compounds of Formula (17), (18) and/or (19) selected fraction no. 5 and selected fraction no. 6 are preferably combined and subjected to a classical column chromatography with a C18 reverse phase with eluting solvents comprising water and an aliphatic $C_1$ to $C_3$ alcohol, most preferably with methanol-water and a gradient of 9:1 to 6:4.

For isolating one or more of the compounds of Formula (1), (5), (6), (7), (20), (25) and/or (29) selected fraction no. 7 is subjected to a classical column chromatography with a C18 reverse phase and eluting solvents comprising at least two of water, an aliphatic $C_1$ to $C_3$ alcohol or a $C_2$ to $C_4$ ketone, in particular with methanol-water with a gradient of 0:100 to 100:0 and subsequently with methanol-acetone with a gradient of 100:0 to 50:50.

Preferably, 12 subfractions are obtained in particular as described above for the first chromatographic separation step. Namely 12 subfractions (referenced as "selected subfraction no. 1" to "selected subfraction no. 12") are preferably selected based on TLC behavior from collected subfractions collected based on a specific volume, i.e. such as that each collected fractions has a volume of 100 ml to 250 ml.

The 12 selected subfractions are then preferably subjected to HPLC with an organic nitrile and water, in particular with acetonitrile-water. From selected subfraction no. 4 one or both of compounds of Formula (25) or (5) can be isolated, from selected subfraction no. 6, one or more of compounds of Formula (6), (7) or (29), and from selected subfractions no. 8 one or both of compounds of Formula (1) and (20) can be obtained.

For isolation of one or more of compounds of Formula (8), (9) and/or (10), selected fraction no. 8 is preferably subjected to MPLC with eluting solvents comprising water and an aliphatic $C_1$ to $C_3$ alcohol, in particular with water-methanol with a gradient of preferably 20% methanol at 0 min, 60% methanol at 45 min and 80% methanol at 65 min and subsequently to HPLC with an organic nitrile and water, in particular with acetonitrile-water in particular 30:70.

For isolation of one or more of compounds of Formula (11), (12), (13), (27) and/or (28) selected fraction no. 11 is preferably subjected to MPLC with eluting solvents comprising water and an aliphatic $C_1$ to $C_3$ alcohol, in particular with water-methanol with a gradient of preferably 20% methanol at 0 min, 60% methanol at 45 min and 80% methanol at 65 min) and subsequently to HPLC with an organic nitrile and water like acetonitrile-water in particular 30:70.

For isolation of the compound of Formula (30) selected fraction no. 12 is preferably subjected to MPLC with eluting solvents comprising water and an aliphatic $C_1$ to $C_3$ alcohol, in particular with water-methanol with a gradient of preferably 20% methanol at 0 min, 60% methanol at 45 min and 80% methanol at 65 min.

In embodiments, in which the third layer is subjected to the at least first and second chromatographic separation step, in particular one or more of the following ingredients are isolated and optionally purified:
  compound of Formula (2), i.e. baphicacanthin B,
  compound of Formula (14), i.e. acanthaminoside isomer,
  compound of Formula (21), i.e. guaiacylglycerol-β-ferulic acid ether,
  compound of Formula (22), i.e. (2S, 3R, 4S)-lyoniresinol-3α-O-β-D-glucopyranoside,
  compound of Formula (23), i.e. (2R, 3S, 4R)-lyoniresinol-3α-O-β-D-glucopyranoside,
  compound of Formula (24), i.e. (+)-5,5'-dimethoxy-9-O-β-D-glucopyranosyl secoisolariciresinol, and/or
  compound of Formula (26), i.e. β-hydroxy-benzenepentanoic acid.

In embodiments, in which the third layer is subjected to the at least first and second chromatographic separation step, the first chromatographic separation step is preferably carried out by means of a classical column chromatography preferably with column dimensions of about 55×3.5 cm and preferably with a polyaromatic adsorbent resin, more preferably with a styrene-divinylbenzene polymer resin as stationary phase. Preferably, the eluting solvents comprise an aliphatic alcohol, in particular a $C_1$ to $C_3$ aliphatic alcohol, and water. More preferably, methanol-water is used with a gradient of 10:90 to 100:0.

Fractions are preferably collected by volume such as about 100 ml to 250 ml of each fraction for obtaining at least 5, preferably at least 15 "collected fractions" and finally combined based on TLC behavior as described above to yield at least 5, in particular 10 selected fractions (referenced as "selected fraction no. 1" to "selected fraction no. 10" as obtained with the third layer).

In embodiments of the present invention, in which the third layer is subjected to the at least first and second chromatographic separation step, the second chromatographic step preferably comprises at least one of MPLC or HPLC. The stationary phase is preferably selected from silica gel or a reverse phase, in particular a C18 reverse phase. MPLC as second chromatographic separation step is in particular carried out with a C18 reverse phase like RP-18 in particular with a particle size of 40 µm to 63 µm and preferably with column dimensions of about 36×460 mm. HPLC as second chromatographic separation step is preferably carried out with a C18 reverse phase with a particle size of 3 µm to 10 µm like 5 µm or 10 µm and preferably with column dimensions of 250×10 mm or 250×22 mm.

For isolation of at least one of compounds of Formula (2), (14), (21) and/or (26) selected fraction no. 8 as obtained with the third layer is preferably subjected to MPLC with eluting solvents comprising water and an aliphatic $C_1$ to $C_3$ alcohol, in particular with water-methanol with a gradient of preferably 20% methanol at 0 min, 60% methanol at 45 min and 80% methanol at 65 min and subsequently to HPLC with an organic nitrile and water like acetonitrile-water in particular 30:70.

For isolation of at least one of compounds of Formula (22), (23) and/or (24) selected fraction no. 10 as obtained with the third layer is preferably subjected to MPLC with eluting solvents comprising water and an aliphatic $C_1$ to $C_3$ alcohol, in particular with water-methanol with a gradient of preferably 20% methanol at 0 min, 60% methanol at 45 min and 80% methanol at 65 min and subsequently to HPLC with an organic nitrile and water like acetonitrile-water in particular 30:70.

In another aspect, the present invention refers to a compound having Formula (1)

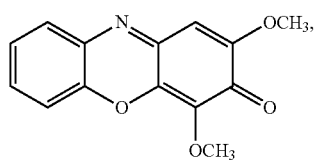

Formula (1)

which can be isolated from *Baphicacanthus cusia* by the method described above. In still another aspect, the present invention refers to a compound having Formula (2)

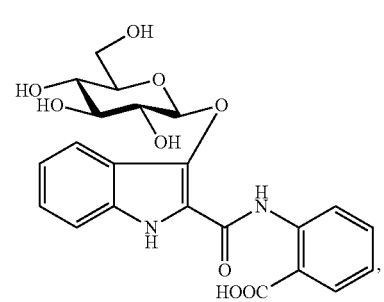

Formula (2)

which can be isolated from *Baphicacanthus cusia* by the method described above.

Further in accordance with the present invention is a composition, preferably a pharmaceutical composition comprising and in particular essentially consisting of:
- at least one, in particular one ingredient, in particular a pharmaceutically effective ingredient, isolated from *Baphicacanthus cusia* according to the method described above, and
- at least one pharmaceutically tolerable excipient such as one or more of a diluent, a filler, a binder, a disintegrant, a lubricant, a coloring agent, a surfactant and a preservative.

The ingredient comprised in the composition, in particular in the pharmaceutical composition, is preferably selected from at least one, more preferably one of:
- compound of Formula (1), i.e. baphicacanthin A,
- compound of Formula (2), i.e. baphicacanthin B,
- compound of Formula (5), i.e. 2-hydroxy-1,4-benzoxazin-3-one,
- compound of Formula (6), i.e. 3-(2'-hydroxyphenyl)-4 (3H)-quinazolinone,
- compound of Formula (7), i.e. 1H-indole-3-carbaldehyde,
- compound of Formula (8), i.e. benzouracil,
- compound of Formula (9), i.e. 2H-1,4-benzoxazin-3-one,
- compound of Formula (11), i.e. acanthaminoside,
- compound of Formula (14), i.e. acanthaminoside isomer,
- compound of Formula (19), i.e. lup-20(29)-en-3β,30-diol,
- compound of Formula (20), i.e. maslinic acid,
- compound of Formula (21), i.e. guaiacylglycerol-β-ferulic acid ether,
- compound of Formula (25), i.e. tyrosol, and/or
- compound of Formula (26), i.e. β-hydroxy-benzenepentanoic acid.

In more preferred embodiments of the present invention, the ingredient is one of:
- compound of Formula (1), i.e. baphicacanthin A,
- compound of Formula (2), i.e. baphicacanthin B,
- compound of Formula (5), i.e. 2-hydroxy-1,4-benzoxazin-3-one,
- compound of Formula (7), i.e. 1H-indole-3-carbaldehyde,
- compound of Formula (9), i.e. 2H-1,4-benzoxazin-3-one, or
- compound of Formula (19), i.e. lup-20(29)-en-3β,30-diol.

In most preferred embodiments of the present invention, the ingredient is one of:
- compound of Formula (5), i.e. 2-hydroxy-1,4-benzoxazin-3-one,
- compound of Formula (7), i.e. 1H-indole-3-carbaldehyde,
- compound of Formula (9), i.e. 2H-1,4-benzoxazin-3-one, or compound of Formula (19), i.e. lup-20(29)-en-3β, 30-diol.

In especially preferred embodiments the ingredient is one of:
compound of Formula (7), i.e. 1H-indole-3-carbaldehyde, or
compound of Formula (19), i.e. lup-20(29)-en-3β, 30-diol.

Most preferably, the ingredient is a compound of Formula (19), i.e. lup-20(29)-en-3β, 30-diol.

The ingredient is contained in the composition, in particular the pharmaceutical composition, preferably in an effective amount, i.e. an amount suitable to treat or prevent a disease in a subject, in particular a human, which also depends on the frequency and number of compositions to be administered.

The skilled person is able to select suitable pharmaceutically tolerable excipients depending on the form of the pharmaceutical composition and is aware of methods for manufacturing pharmaceutical compositions as well as able to select a suitable method for preparing the pharmaceutical composition depending on the kind of pharmaceutically tolerable excipients and the form of the pharmaceutical composition.

The pharmaceutical composition according to the invention can be present in solid, semisolid or liquid form to be administered by an oral, rectal, topical, parenteral or transdermal or inhalative route to a subject, preferably a human.

The pharmaceutical composition may comprise further pharmaceutical effective ingredients such as therapeutic compounds used for treating viral diseases in particular influenza like neuraminidase inhibitors (oseltamivir and zanamivir) and M2 protein inhibitors (adamantane derivatives) or viral polymerase inhibitors like ribavirin. Further in accordance with the present invention is a method of treating a subject suffering from a viral disease comprising administering an effective amount of at least one ingredient, preferably one ingredient, isolated from *Baphicacanthus cusia* according to the method described above to the subject.

In particular, the method comprises administering an affective amount of one of:
compound of Formula (1), i.e. baphicacanthin A,
compound of Formula (2), i.e. baphicacanthin B,
compound of Formula (5), i.e. 2-hydroxy-1,4-benzoxazin-3-one,
compound of Formula (6), i.e. 3-(2'-hydroxyphenyl)-4 (3H)-quinazolinone,
compound of Formula (7), i.e. 1H-indole-3-carbaldehyde,
compound of Formula (8), i.e. benzouracil,
compound of Formula (9), i.e. 2H-1,4-benzoxazin-3-one,
compound of Formula (11), i.e. acanthaminoside,
compound of Formula (14), i.e. acanthaminoside isomer,
compound of Formula (19), i.e. lup-20(29)-en-3β, 30-diol,
compound of Formula (20), i.e. maslinic acid,
compound of Formula (21), i.e. guaiacylglycerol-β-ferulic acid ether,
compound of Formula (25), i.e. tyrosol, or
compound of Formula (26), i.e. β-hydroxy-benzenepentanoic acid.

In more preferred embodiments of the present invention, the active ingredient is one of:
compound of Formula (1), i.e. baphicacanthin A,
compound of Formula (2), i.e. baphicacanthin B,
compound of Formula (5), i.e. 2-hydroxy-1,4-benzoxazin-3-one,
compound of Formula (7), i.e. 1H-indole-3-carbaldehyde,
compound of Formula (9), i.e. 2H-1,4-benzoxazin-3-one, or
compound of Formula (19), i.e. lup-20(29)-en-3β, 30-diol.

In most preferred embodiments of the present invention, the active ingredient is one of:
compound of Formula (5), i.e. 2-hydroxy-1,4-benzoxazin-3-one,
compound of Formula (7), i.e. 1H-indole-3-carbaldehyde,
compound of Formula (9), i.e. 2H-1,4-benzoxazin-3-one, or
compound of Formula (19), i.e. lup-20(29)-en-3β, 30-diol.

In especially preferred embodiments, the active ingredient is one of:
compound of Formula (7), i.e. 1H-indole-3-carbaldehyde, or
compound of Formula (19), i.e. lup-20(29)-en-3β, 30-diol.

Most preferably, the active ingredient is a compound of Formula (19), i.e. lup-20(29)-en-3β, 30-diol.

The subject is an animal or human, preferably it is a mammal and most preferably a human. The expression "effective amount" generally denotes an amount sufficient to produce therapeutically desirable results, wherein the exact nature of the result varies depending on the specific disorder which is treated. When the disorder is a viral disease, the result is usually an inhibition or suppression of the replication of the virus and/or suppression and/or prevention of virus-induced cytopathic affects.

The effective amount of the active ingredient isolated from *Baphicacanthus cusia* may depend on the $IC_{50}$, the species, body weight, age and individual conditions of the subject and can be determined by standard procedures such as with cell cultures or experimental animals. Amounts of between 1 mg/kg and 50 mg/kg body weight as effective for ritonavir such as 5 mg/kg, 10 mg/kg or 30 mg/kg can be used. The concentration of the ingredient isolated from *Baphicacanthus cusia* may be between 5 and 300 µM.

The viral disease is preferably caused by a RNA virus, i.e. a virus that has RNA (ribonucleic acid) as its genetic material. More preferably, the viral disease is caused by an influenza virus, in particular an Influenza type A virus such as one or more of the subtypes H3N2, H5N1 or H1N1, most preferably Influenza A virus subtype H1N1. Most preferably, the viral disease is influenza caused by Influenza A virus subtype H1N1.

The present invention also refers to a method of treating a subject suffering from a viral disease comprising administering an effective amount of a compound having one of the following Formulas to the subject:
compound of Formula (5), i.e. 2-hydroxy-1,4-benzoxazin-3-one,
compound of Formula (7), i.e. 1H-indole-3-carbaldehyde,
compound of Formula (9), i.e. 2H-1,4-benzoxazin-3-one, or
compound of Formula (19), i.e. lup-20(29)-en-3β, 30-diol.

I.e. a compound of one of these Formulas is administered as monotherapy by solely administering said single compound or alternatively in combination with one of a neuraminidase inhibitor (oseltamivir and zanamivir), a M2 protein inhibitor (adamantane derivatives) or a viral polymerase inhibitor like ribavirin.

Preferably, the compound has:

Formula (7), i.e. 1H-indole-3-carbaldehyde, or

Formula (19), i.e. lup-20(29)-en-3β, 30-diol.

The subject is preferably a mammal and most preferably a human. The effective amount could be, for example, between 1 mg/kg and 50 mg/kg body weight as effective for ritonavir such as 5 mg/kg, 10 mg/kg or 30 mg/kg. The concentration of the ingredient isolated from *Baphicacanthus cusia* may be between 5 and 300 μM.

The viral disease is preferably caused by an influenza virus, in particular by one of the subtypes H3N2, H5N1 or H1N1, most preferably by the subtype H1N1.

Another aspect relates to a method of treating a viral disease comprising isolating and optionally purifying an ingredient from *Baphicacanthus cusia* by the method described above, in particular one of the ingredients having Formula (1), (2), (5), (7), (9) or (19), further preferred having Formula (5), (7), (9) or (19); and formulating the ingredient into a pharmaceutically composition; and administering said pharmaceutical composition to a subject suffering from the viral disease, in particular Influenza type A, more preferably Influenza type A subtype H1N1. The subject is preferably a human.

EXAMPLES

Example 1

Example 1A

Materials Used and Conditions Applied

Thin layer chromatography (TLC): Kieselgel 60 $F_{254}$ plates (0.2 mm thick, Merck KGaA Corporation); visualized by UV light (254 and 366 nm) and by spraying with 10% $H_2SO_4$ reagent.

Column chromatography (CC): silica gel 60 (200-300 mesh, Merck KGaA Corporation) and Reverse Phase-18 (RP-18) (45 μm, Merck KGaA Corporation).

Medium Pressure Preparative Liquid Chromatography: BUCHI MPLC System using a RP-18 column (SilicBond C18, 36×460 mm ID, 40-63 μm particle size (Silicycle)). Preparative and semi-preparative HPLC: Lab Alliance system with a YMC-Pack ODS-A column (10 μm, 250×10 mm) and a Vision HT C18 polar column (5 μm, 22×250 mm, Grace, USA).

Optical rotations: Rudolph Research Analytical Autopol I automatic polarimeter (Na 589 nm); in methanol. $^1$H- and $^{13}$C-NMR spectra: A Bruker Ascend 600 NMR spectrometer (600 and 150 MHz, resp.); in $CD_3OD$ and Pyridine-$d_5$; at ambient temp; coupling constants J in Hz, and chemical shifts in δ [ppm]. HR-ESI-MS: Agilent 6230 accurate mass time-of-flight mass spectrometer (USA) equipped with an electrospray ion source (ESI), coupled to an UHPLC system performed on an Agilent 1290 system using an Eclipse XDB-C18 column (3.0×150 mm, Agilent); in m/z.

The root of *Baphicacanthus cusia* (Nees) Bremek was collected from Honghe, Yunnan, China in October 2012. The plant was authenticated by Dr. Zhifeng Zhang (Macau University of Science and Technology). MDCK cells and influenza virus A/PR/8/34 (H1N1) were purchased from the American Tissue Culture Collection (ATCC).

Example 1B

Isolation of Ingredients from *Baphicacanthus cusia*

Air-dried roots of *Baphicacanthus cusia* (Nees) Bremek (3 kg) were cut into small pieces and refluxed with 80% aqueous ethanol (30 L, 24 L, 18 L). The extract was suspended in water, and partitioned with ethyl acetate (1 L each) and n-butanol (1 L each) successively to yield the ethyl acetate layer (44 g), n-BuOH layer (48 g) and $H_2O$ layer (62 g).

The ethyl acetate layer was subjected to silica gel CC (35×5 cm) using a gradient mixture of ethyl acetate-petroleum ether (9:1 to 5:5) as eluent to afford selected fractions (Fr.) 1-13, wherein the fractions were collected by volume and finally combined based on TLC behavior to give 13 selected fractions. Fr. 3 (6.84 g) was purified by CC over silica gel (n-hexane-ethyl acetate=9:1 to 5:5) to yield compound of Formula (15) (2.3 g). Fr. 4 (3.0 g) was subjected to chromatography on RP-18 CC (methanol-$H_2O$=9:1 to 7:3) and silica gel CC (n-hexane-ethyl acetate=9:1 to 6:4) to yield compounds of Formula (3) (2.3 mg), (4) (3.2 mg) and (16) (4.0 mg). The combined Fr. 5 (1.2 g) and Fr. 6 (0.6 g) were separated by RP-18 CC (methanol-$H_2O$=9:1 to 6:4) to yield compounds of Formula (17) (2.0 mg), (18) (3.0 mg), and (19) (3.0 mg). Fr. 7 (2.0 g) was separated by RP-18 CC with methanol-$H_2O$ (0:100 to 100:0) and methanol-$CH_3COCH_3$ (100:0 to 50:50) to give 12 selected subfractions, wherein the subfractions were collected by volume and finally combined based on TLC behavior to give 12 selected subfractions (sub Fr.) 7-1 to 7-12. Sub Fr. 7-4 (71.0 mg) afforded compounds of Formula (25) (1.0 mg) and (5) (2.0 mg), sub Fr. 7-6 (54.0 mg) afforded compounds of Formula (6) (1.5 mg), (29) (1.0 mg) and (7) (1.5 mg) and sub Fr. 7-8 (63.0 mg) afforded compounds of Formula (1) (1.5 mg) and (20) (2.0 mg), all by semi-preparation HPLC (actetonitrile-$H_2O$). Fr. 8 (1.4 g) was separated by MPLC (eluents A: $H_2O$, B: methanol, gradient: B 20% at 0, B 60% at 45 min, B 80% at 65 min) and semi-preparative HPLC eluted with acetonitrile-$H_2O$ (30:70) to obtain compounds of Formula (8) (1.5 mg), (9) (1.0 mg) and (10) (1.0 mg). Fr. 11 (1.7 g) was separated by MPLC (eluents A: $H_2O$, B: methanol, gradient: B 20% at 0, B 60% at 45 min, B 80% at 65 min) and semi-preparative HPLC eluted with actetonitrile-$H_2O$ (30:70) to obtain compounds of Formula (11) (2.1 mg), (27) (5.0 mg), (28) (1.0 mg), (12) (2.0 mg), and (13) (1.5 mg). Fr. 12 (0.9 g) was separated by MPLC (eluents A: $H_2O$, B: methanol, gradient: B 20% at 0, B 60% at 45 min, B 80% at 65 min) to afford compound of Formula (30) (5.1 mg).

The n-butanol layer (48 g) was chromatographed on MCI CHP20P (55×3.5 cm; analytical TLC control) eluting with 2 L mixtures of methanol-$H_2O$ (10:90 to 100:0) to give Fr. 1-10, wherein the fractions were collected by volume (100-250 ml) and finally combined based on TLC behavior to give 10 selected fractions. Fr. 8 (1.4 g) was separated by MPLC (eluents A: $H_2O$, B: methanol, gradient: B 20% at 0, B 60% at 45 min, B 80% at 65 min) and preparative HPLC eluted with acetonitrile-$H_2O$ (30:70) to obtain compounds of Formula (14) (1.0 mg), (21) (1.0 mg), (2) (2.0 mg) and (26) (1.0 mg). Fr. 10 (1.5 g) was separated by MPLC (eluents A: $H_2O$, B: methanol, gradient: B 20% at 0, B 60% at 45 min, B 80% at 65 min) and preparative HPLC eluted with acetonitrile-$H_2O$ (30:70) to yield compounds of Formula (22) (0.5 mg), (23) (1.0 mg) and (24) (1.5 mg).

The chemical structures of these compounds ((1) and (2)) were elucidated on the basis of 1D/2D NMR and HR-MS spectral evidence.

Compound of Formula (1) was obtained as brown yellow amorphous powder. Its HR-ESI-MS showed a positive pseudo-molecular ion peak at m/z 258.0769 ([M+H]$^+$; calc. 258.0761), corresponding to $C_{14}H_{12}NO_4$ having 9 degrees of unsaturation. The
$^1$H-NMR spectrum suggested the presence of one 1,2-disubstituted benzene ring (δ(H) 7.82 (dd, J=1.5, 8.0); δ(H) 7.62 (td, J=1.6, 8.0); δ(H) 7.47 (td, J=1.4, 8.0); δ(H) 7.54 (dd, J=1.2, 8.0 Hz)), an olefinic proton (δ(H) 6.76 (s)) and two methoxyl groups (δ(H) 4.00 (s) and 4.01(s)). From the above evidence, the compound of Formula (1) was supposed to be analogous to questiomycin A (Kinjo J. E. et al., Tetrahedron Lett. 1987, 28, 3697). The $^{13}$C-NMR spectrum of the compound of Formula (1) showed total 14 carbons signals. While $^{13}$C-NMR signals of the A-ring of the compound of Formula (1) were good in accordance with those of questiomycin A, a significant change was observed on the C-ring. Heteronuclear Multiple Bond Correlations (HMBC) of H-1' (δ(H) 4.00 (s)) to C-2 (δ(C) 156.8) and H-2' (δ(H) 4.01 (s)) to C-4 (δ(C) 136.1) indicated the methoxyl group 1'-OMe was located at C-2 and 2'-OMe was located at C-4. Consequently, the compound of Formula (1) was determined as 2,4-dimethoxyl-3H-phenoxazin-3-one and named as baphicacanthin A (see FIG. 1). Baphicacanthin A (=2,4-dimethoxyl-3H-phenoxazin-3-one; compound of Formula (1)).
$^1$H-NMR (CD$_3$OD, 600 MHz): δ6.76 (s, 1H, H-1), 7.82 (dd, J=1.5, 8.0 Hz, 1H, H-6), 7.62 (td, J=1.6, 8.0 Hz, 1H, H-7), 7.47 (td, J=1.4, 8.0 Hz, 1H, H-8), 7.54 (dd, J=1.2, 8.0 Hz, 1H, H-9), 4.00 (s, 3H, H-1'), 4.01 (s, 3H, H-2'). $^{13}$C-NMR (CD$_3$OD, 150 MHz): δ104.2 (C-1), 156.8 (C-2), 175.9 (C-3), 136.1 (C-4), 138.0 (C-4a), 143.3 (C-5a), 129.4 (C-6), 131.2 (C-7), 125.4 (C-8), 116.3 (C-9), 133.5 (C-9a), 148.4 (C-10a), 56.5 (C-1'), 60.9 (C-2'). HR-ESI-MS: 258.0769 ([M+H]$^+$, $C_{14}H_{13}NO_4^+$; calcd. 258.0761).

Figure 2:
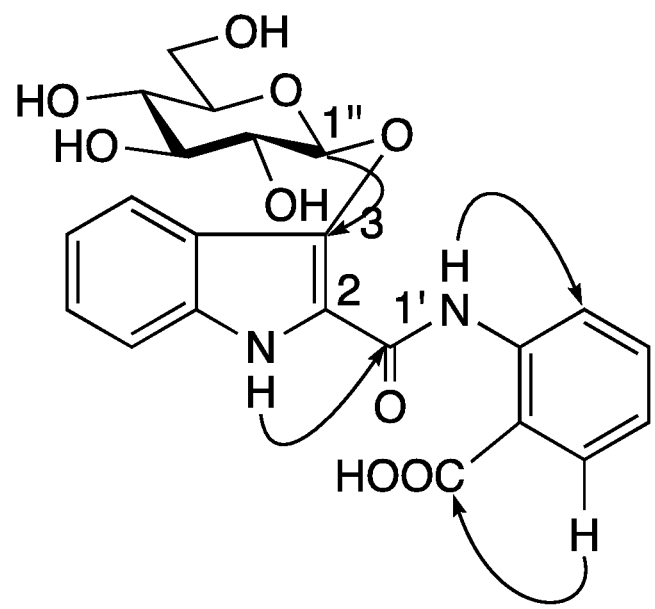
FIG. 2 shows selected HMBC correlations of baphicacanthin B (compound of Formula (2).

Compound of Formula (2) was obtained as yellow amorphous powder, [a]$_D^{25}$+55.7 (c=0.620, methanol). Its HR-ESI-MS displayed a pseudo-molecular ion peak at m/z 457.1233 ([M–H]$^-$; calc. 457.1253), corresponding to $C_{22}H_{22}N_2O_9$ having 9 degrees of unsaturation. The anomeric proton at δ(H) 5.27 (d, J=7.7 Hz, 1H), with the C-atoms at δ(C) 62.7, 71.3, 73.6, 77.8, 78.3 and 105.4 were indicative of a β-glucopyranosyl moiety. The $^1$H-NMR and $^{13}$C-NMR resonances corresponding to the aglycone moiety consisted of substituted indole (δ(H) 12.98 (s), δ(H) 7.90 (d, J=8.0), δ(H) 7.09 (t, J=8.0), δ(H) 7.27 (t, J=8.0), δ(H) 7.43 (d, J=8.0) and δ(C) 120.2, 138.8, 120.9, 119.9, 121.6, 126.1, 113.5, 135.8) and O-carboxamide benzoate δ(H) 12.75 (s), δ(H) 8.09 (d, J=8.0), δ(H) 7.58 (t, J=8.0), δ(H) 7.19 (t, J=8.0), δ8.71 (d, J=8.0) and δ(C) 161.5, 141.8, 119.9, 132.3, 123.9, 134.4, 122.9, 171.2). The HMBC correlation observed between H-1 (δ(H) 12.98 (s)) and C-1' (δ(C) 141.8) suggested that the O-carboxamido benzene moiety linked with C-2 of indole. The position of the glucosyl unit at C-3 was supported by the HMBC correlation between H-1" (δ(H) 5.27 (d, J=7.7)) and C-3 (δ(C) 138.8). Therefore, the compound of Formula (2) was elucidated as 2-[[[(3-β-D-glucopyranosyloxy)-1H-indol-2-yl]carbonyl]amino]-benzoic acid and named as baphicacanthin B (Wu P. L. et al., J. Nat. Prod. 2006, 69, 1467), see also FIG. 2.

Baphicacanthin B (=2-[[[(3-β-D-glucopyranosyloxy)-1H-indol-2-yl]carbonyl]amino]-benzoic acid; compound of Formula (2)). White amorphous powder.
[a]$_D^{25}$+55.7 (c 0.620, MeOH). $^1$H-NMR (Pyridine-d$_5$, 600 MHz): δ 12.98 (s, 1H, H-1), 7.90 (d, J=8.0 Hz, 1H, H-5), 7.09 (t, J=8.0 Hz, 1H, H-6), 7.27 (t, J=8.0 Hz, 1H, H-7), 7.43 (d, J=8.0 Hz, 1H, H-8), 12.75 (s, 1H, H-2'), 8.09 (d, J=8.0 Hz, 1H, H-4), 7.58 (t, J=8.0 Hz, 1H, H-5'), 7.19 (t,J=8.0 Hz, 1H, H-6'), 8.71 (d, J=8.0 Hz, 1H, H-7'), 5.27 (d, J=7.7 Hz, 1H, H-1"), 3.89 (m, 1H, H-2"), 3.51 (t, 8.7 Hz, 1H, H-3"), 3.39 (m, 2H, H-4"), 3.42 (t, J=8.7 Hz, 1H, H-5"), 3.61 (d, J=5.0 Hz, 1H, H-6"α), 3.80 (dd, J=11.7, 2.3 Hz, 1H, H-6"β). $^{13}$C-NMR (Pyridine-d$_5$, 150 MHz): 120.2 (C-2), 138.8 (C-3), 120.9 (C-4), 119.9 (C-5), 121.6 (C-6), 126.1 (C-7), 113.5 (C-8), 135.8 (C-9), 161.5 (C-1'), 141.8 (C-3'), 119.9 (C-4'), 132.3 (C-5'), 123.9 (C-6'), 134.4 (C-7'), 122.9 (C-8'), 171.2 (C-9'), 105.4 (C-1"), 74.6 (C-2"), 77.8 (C-3"), 71.3 (C-4"), 78.3 (C-5"), 62.7 (C-6"). HR-ESI-MS: 457.1293 ([M–H]$^-$, $C_{22}H_{20}N_2O_9^-$; calcd. 457.1253).

On the basis of the comparison of their NMR spectroscopic data further 28 compounds were identified to be 2-benzoxazolinone (3) (Singh M. S., Indian. J. Chem. 2007, 46, 1666), tryptanthrin (4) (Liu Y. et al., Chin. J. Med. Chem. 2009, 19, 273), 2-hydroxy-1,4-benzoxazin-3-one (5) (Macias F. A. et al., J. Agr. Food. Chem. 2006, 54, 991), 3-(2'-hydroxyphenyl)-4(3H)-quinazolinone (6) (Liu Y. H., Qin G. W., Chin. Tradit. Herb. Drugs. 2002, 33, 97), 1H-indole-3-carbaldehyde (7) (Ashour M. A. et al., Arkivoc. 2007, 40, 225), benzouracil (8) (Xiao Y. et al., RSC Adv. 2014, 5, 5032.), 2H-1,4-benzoxazin-3-one (9) (Ramesh, Chintakunta, et al. Tetrahedron, 2011, 6,1187), 3-carboxy-indole (10) (Ma, Q. Y., et al., Afr J Microbial Res. 2013, 7, 1543.), acanthaminoside (11) (Amer M. E. et al., J. Brazil. Chem. Soc. 2004, 15, 262), 4(3H)-quinazolinone (12) (Roopan, S. M. et al., Can. J. Chem. 2008, 86, 1019), deoxyvasicinone (13) (Potewar T. M. et al., ARKIVOC. 2008, 14, 100), acanthaminoside isomer (14) (Amer M. E. et al., J. Brazil. Chem. Soc. 2004, 15, 262), lupeol (15) (Fotie J. Et al., J. Nat. Prod. 2006, 69, 62), betulin (16) (Siddiqui S. et al., J. Nat. Prod. 1988, 51, 229), betulinic acid (17) (Awan Z. I. et al., IOSR J. Appl. Chem. 2013, 5, 2278), ursolic acid (18) (Silva M. G. V. et al., Molecules. 2008, 13, 2482), lup-20(29)-en-3β, 30-diol (19) (Abdel-Mogib M., Phytochemistry. 1999, 51, 445), maslinic acid (20) (Shoko T. et al., Phytochemistry. 2002, 59, 315), guaiacylglycerol-β-ferulic acid ether (21) (Tao S. H. et al., J. Chin. Med. Mat. 2009, 32, 712), (2S, 3R, 4S)-Iyoniresinol-3α-O-β-D-glucopyranoside (22) (Sun G. et al., J. Med. Plants. Res. 2012, 6, 2200), (2R, 3S, 4R)-Iyoniresinol-3α-O-β-D-glucopyranoside (23) (Sun G. et al., J. Med. Plants. Res. 2012, 6, 2200), (+)-5,5'-dimethoxy-9-O-β-D-glucopyranosyl secoisolariciresinol (24) (Shibuya H. et al., Chem. Pharm. Bull. 1992, 40, 2639), tyrosol (25) (Owen R. W. Et al., Clin. Chem. 2000, 46, 976), β-hydroxy-benzenepentanoic acid (26) (Sandoval A. et al., Appl. Microbiol. Biot. 2005, 67, 97), acteoside (27) (Kobayashi H. et al., Chem. Pharm. Bull. 1987, 35, 3309), acteoside isomer (28) (Kobayashi H. et al., Chem. Pharm. Bull. 1987, 35, 3309), loliolide (29) (Machida K., Kikuchi M., Phytochemistry. 1996, 41, 1333) hispiduloside (30) (Weng X. C. Wang W., Food. Chem. 2000, 71, 489). Among these, compounds 3-14 belong to alkaloids, 15-20 belong to triterpenoids, 21-24 belong to lignans, 25-28 belong to phenylethanoids, 29 is a sesquiterpene lactone and 30 is a flavonoid.

Compounds of Formula (5) to (9), (11), (14), (19), (20), (21), (25) and (26) were isolated from Baphicacanthus cusia for the first time.

Example 2

Anti-viral efficacy of isolated ingredients from Baphicacanthus cusia by means of a biological assay (Viral cytopathic effect (CPE) assay)

Anti-influenza virus activity was evaluated by cytopathic effect (CPE) inhibition assay.

MDCK cells were seeded into 96-well plates at a density of 5,000 cells per well and incubated overnight in a humidified 5% $CO_2$ incubator at 37° C. Next day, MDCK cells were infected with $100TCID_{50}$ of influenza A/PR/8/34 (H1N1) virus at 37° C. for 2 h. Then, the inoculum was removed and the cells were treated with the desired concentration of the selected isolated ingredients (5-300 μM) or ribavirin (5-400 μM) in serum-free DMEM with 1.5 μg/ml of L-(1-tosylamido-2-phenyl) ethyl chloromethyl ketone (TPCK)-treated trypsin (Sigma). The virus-induced cytopathic effects were observed under microscope and the 50% inhibitory concentration ($IC_{50}$) was calculated with the Reed-Muench method.

Four selected compounds and ribavirin were assayed. MDCK cells were infected with influenza virus ($100TCID_{50}$), and then isolated ingredients were added at various concentrations. After treatment for 48 h, the antiviral effect of each compound was evaluated. As shown in Table 2, compounds 1H-indole-3-carbaldehyde (compound of Formula (7)) (42 μM) and lup-20(29)-en-3β, 30-diol (compound of Formula (19)) (33.61 μM) exhibited exceptional antiviral activity against influenza virus A/PR/8/34 (H1N1).

TABLE 2 anti-viral activity of selected ingredients isolated from *Baphicacanthus cusia*

| Compound of Formula | | | | |
|---|---|---|---|---|
| 5 | 7 | 9 | 19 | ribavirin |
| $IC_{50}$ (μM) >200 | 42 | >200 | 33.61 | 30.43 |

The invention claimed is:

1. A method of treating a subject suffering from a viral disease comprising administering to the subject an amount between 1mg-kg and 50mg/kg body weight of a compound selected from the group consisting of:

a compound of Formula (5)

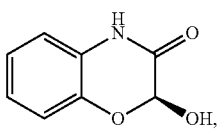

Formula (5)

a compound of Formula (9)

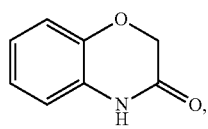

Formula (9)

and a compound of Formula (19)

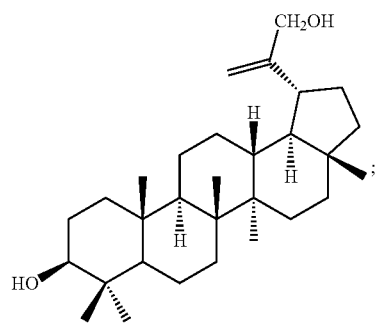

Formula (19)

and wherein the viral disease is caused by an Influenza A virus.

2. The method of claim 1, wherein the Influenza A virus is selected from subtypes H3N2, H5N1 or H1N1.

3. The method of claim 1, wherein the Influenza A virus is Influenza A virus subtype H1N1.

4. A method of treating a subject suffering from a viral disease comprising administering an amount between 1mg/kg and 50mg/kg body weight of a compound having Formula (19) to the subject:

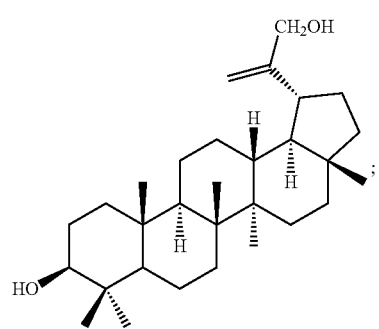

Formula (19)

wherein the viral disease is caused by an Influenza A virus.

5. The method of claim 4, wherein the Influenza A virus is selected from subtypes H3N2, H5N1 or H1N1.

* * * * *